United States Patent [19]
Keely et al.

[11] Patent Number: 5,482,608
[45] Date of Patent: Jan. 9, 1996

[54] CAPILLARY ELECTROPHORESIS FLOW CONTROL SYSTEM

[75] Inventors: Catherine A. Keely, Cupertino; Douglass McManigill, Palo Alto; Robert R. Holloway, Montara, all of Calif.

[73] Assignee: Hewlett Packard Company, Palo Alto, Calif.

[21] Appl. No.: 6,353

[22] Filed: Jan. 19, 1993

[51] Int. Cl.[6] .................................................. C25B 9/00
[52] U.S. Cl. ............................. 204/299 R; 204/180.1; 204/182.8; 356/344
[58] Field of Search .................... 204/180.1, 182.5, 204/299 R; 356/344

[56] References Cited

U.S. PATENT DOCUMENTS

| | | | |
|---|---|---|---|
| 3,705,845 | 12/1972 | Everaerts | 204/299 R |
| 3,869,365 | 3/1975 | Sunden | 204/180 |
| 4,906,344 | 3/1990 | Hjerten | 204/299 R |
| 5,061,361 | 11/1991 | Gordon | 204/299 R |
| 5,302,264 | 4/1994 | Welch et al. | 204/180.1 |

FOREIGN PATENT DOCUMENTS

0395796  11/1990  European Pat. Off.

OTHER PUBLICATIONS

Ravindra Datta, Veerabhadra R. Kota Marthi, "Electrokinetic Dispersion In Capillary Electrophoresis," Jun. 1990, vol. 36, No. 6, pp. 916–926.

CA 113 (23): 207828y, Single–stranded RNA molecular weight and shape determination by differential pressure capillary viscometry, sedimentation velocity, and gel electrophoresis.

CA 113 (26): 238658x, High Pressure and Super–critical Capillary Electrophoresis.

Everaerts et al., Journal of Chromotography, 60:397–405 (1971).

Everaerts et al., Journal of Chromotography, 19:262–268 (1970).

*Primary Examiner*—John Niebling
*Assistant Examiner*—C. Delacroix Muirheid

[57] ABSTRACT

A system for controlling the bulk flow rate in capillary electrophoresis employs pressure to increase velocity without unacceptably increasing plate height. Thus, the system controls bulk flow over a range of velocities, independent of the chemistry of the system. Additionally, the use of pressure under certain conditions may decrease plate height and improve resolution.

12 Claims, 4 Drawing Sheets

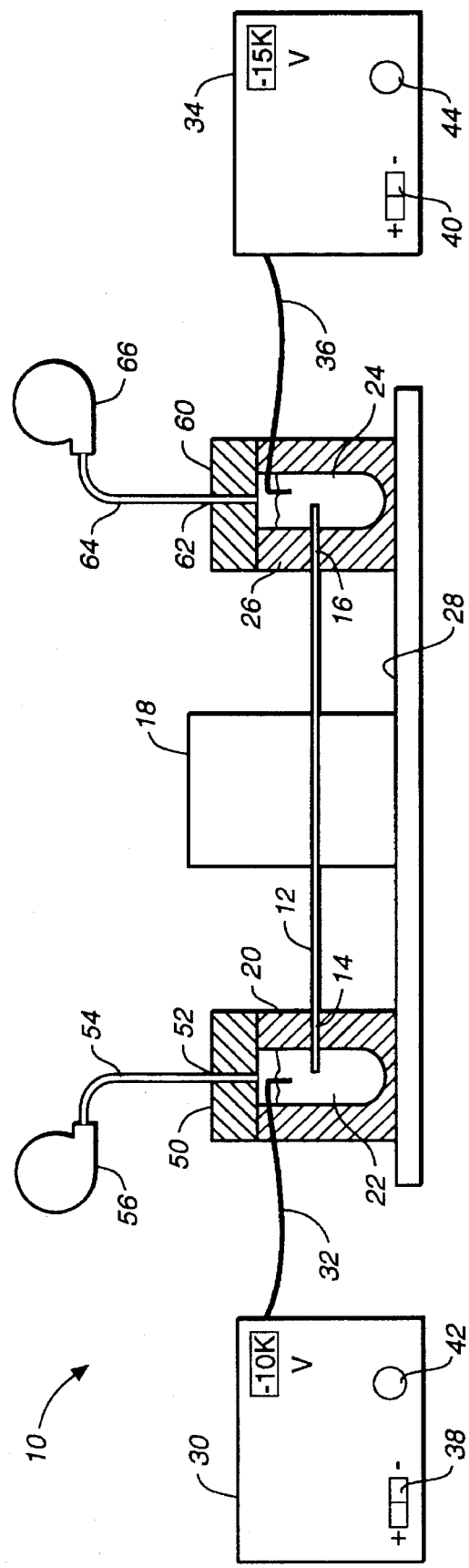
FIG._1

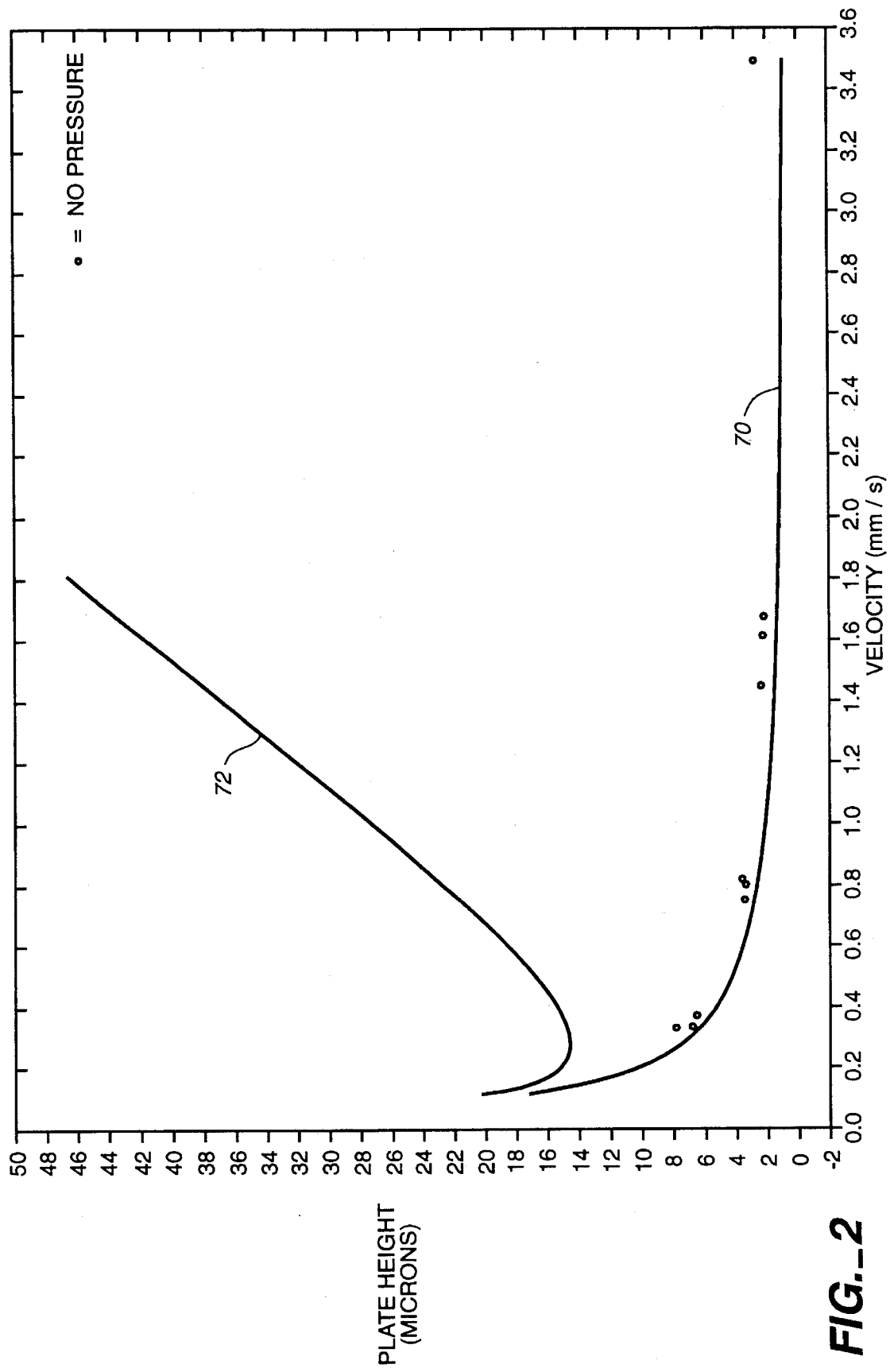
FIG._2

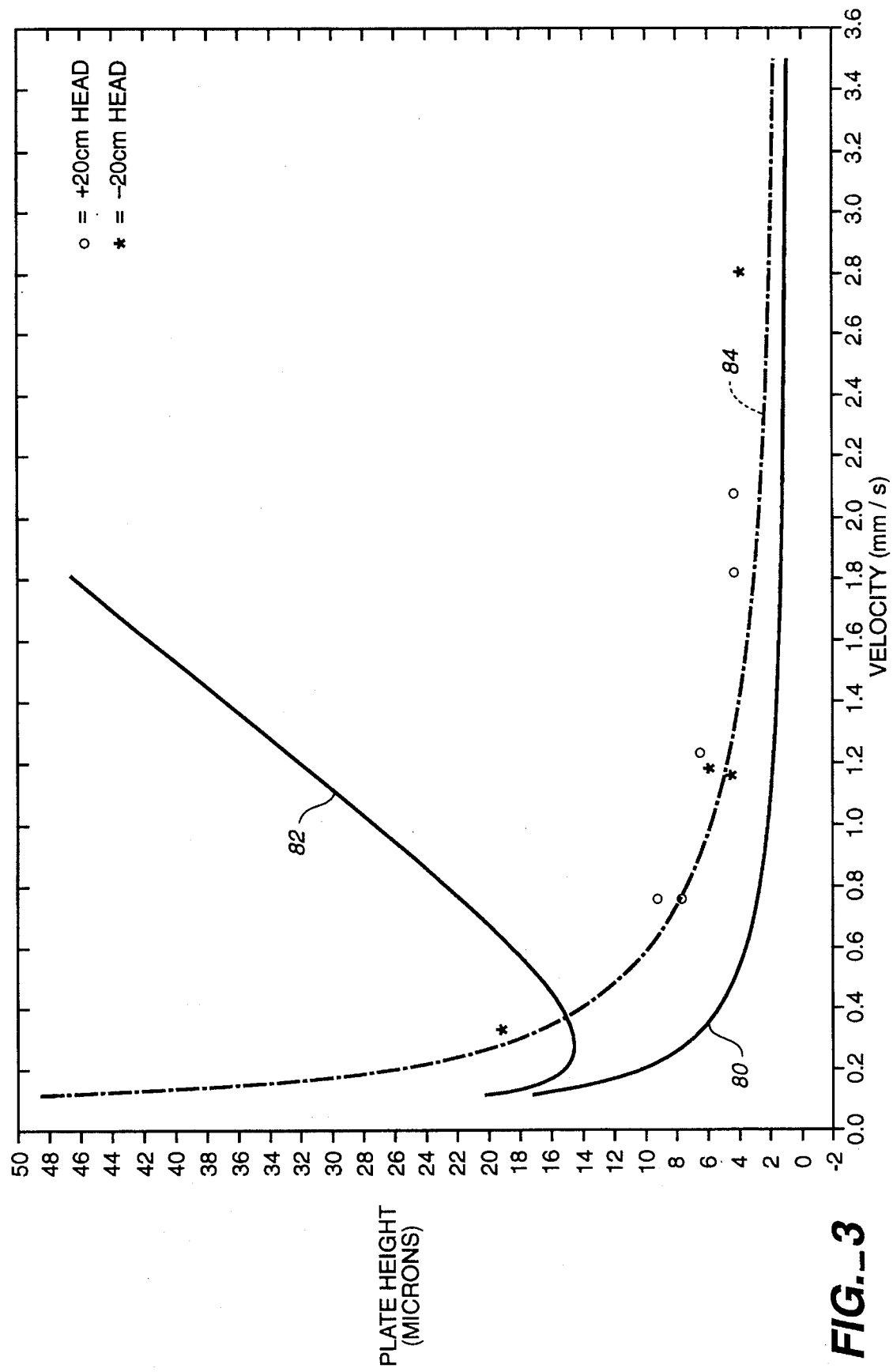
FIG._3

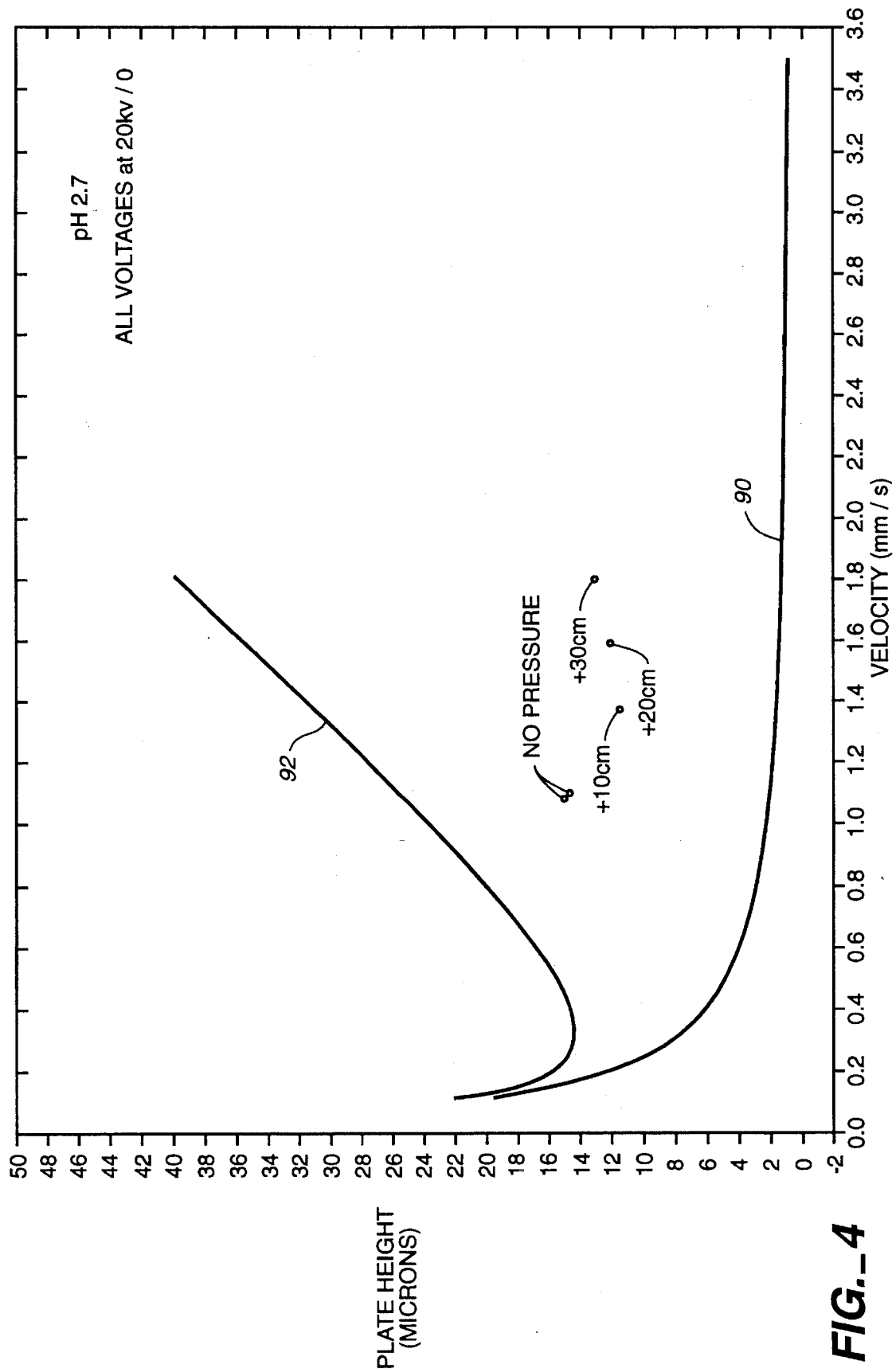
FIG._4

CAPILLARY ELECTROPHORESIS FLOW CONTROL SYSTEM

BACKGROUND OF THE INVENTION

1. Field of the Invention

The present invention relates generally to capillary electrophoresis and, more particularly, to systems for controlling the bulk flow in capillary electrophoresis.

2. State of the Art

Electrophoresis is well known as an analytical technique for separating and detecting constituents in a sample. Electrophoretic techniques are based upon the fact that each molecular species has a unique combination of mass, size, shape, charge, density and sub-unit structure, all of which may result in mobility differences responsive to an electric field. Various electrophoretic techniques use one or more of these properties to cause varying degrees of separation via the migration of molecular species in the presence of an electric field. Applications for electrophoresis include the determination of sample purity, the determination of molecular weights for proteins and nucleic acids, the mapping of nucleic acid primary structure (e.g., DNA and RNA sequence analyses) and the definition of phenotypic variance of a protein at the molecular level.

Capillary electrophoresis is an electrophoretic technique that employs a capillary tube which is filled with a conductive fluid. In practicing capillary electrophoresis, a small quantity of sample is introduced at one end of the capillary tube, and a potential difference is applied across the ends of the tube. Then, under the influence of the potential difference, electroosmotic flow and differences in electrophoretic mobilities combine to provide a spatial separation of constituents of the sample solution. That is, when a positive electrode is applied to the inlet end of the capillary tube and a ground electrode is applied to the outlet end, spatial separation can be achieved, for example, with positively charged constituents exiting first, followed by neutral constituents and then negatively charged constituents. Each constituent of a sample can be detected by identifying the time required for the constituent to travel through the capillary tube.

Electroosmotic flow is the movement of a liquid relative to a stationary charged surface as a result of an electric field applied to the liquid. It has been explained that electroosmotic flow is a result of charge accumulation at the capillary surface due to chemical equilibrium of the interior surface of the capillary and the electrolyte. The charge of the surface attracts a thin layer of oppositely charged electrolyte ions, which accumulate adjacent to the inner surface. The longitudinally extending electric field that is applied across the capillary tube accelerate the positive ions which are hydrated by water toward a grounded outlet end of the capillary tube, viscously dragging other hydrated molecules. The result is a bulk flow of the sample in the buffer solution toward the grounded outlet end of the capillary tube. Consequently, electroosmotic flow provides a means for moving neutral and negatively charged constituents of a sample toward a ground electrode.

Electrophoretic migration is the movement of charged constituents in response to an electric field. Thus, under the influence of an electric field, a positively charged molecule will be accelerated through the fluid toward the cathode. Under the same circumstances, negatively charged molecules are repelled by the cathode, but the force of the electroosmotic flow may overcome the repulsion and advance the negatively charged molecules.

In practice, the quantity of a constituent within a sample can be determined by the area of a signal trace of an electropherogram during a period of detection of that constituent. Such detection is usually accomplished by placing ultraviolet detectors at the outlet end of the capillary tube, but other placement and detectors are known. In such systems, plate height is a measure of the sharpness of the flow front as measured by the shape of the sample signal. A lower plate height corresponds to a sharper flow front. In general, it is desirable to have a small plate height since plate height is inversely related to the resolution of a capillary electrophoresis system.

In summary, it is known that the voltage difference in a capillary electrophoresis system, when applied to charged molecules, moves these molecules through the system. This phenomenon is known as electrophoretic flow or electrophoretic migration. Electroosmotic flow, on the other hand, is a bulk flow phenomenon in that this is when the solution moves from one end of the capillary electrophoresis system to the other. Electroosmotic flow is a function of the capillary surface charge and the voltage difference, among other factors. In practice, varying electroosmotic flow is one means of controlling bulk flow but it is dependent on the chemistry of the system in use. Furthermore, electroosmotic flow alone cannot be controlled over a range of velocities as easily as pressure. For example, for a capillary with a fused silica surface at pH 7, the electroosmotic flow cannot be adjusted by external means independent of the electrophoretic migration.

What is needed is a method for controlling bulk flow which can be applied over a range of velocities. Furthermore, such a method should be independent of chemistry to permit its application to many situations.

SUMMARY OF THE INVENTION

Generally speaking, the present invention provides a capillary electrophoresis system for controlling bulk flow over a range of velocities and independent of chemistry while maintaining a sharp flow front. More particularly, the present invention provides a system for controlling the bulk flow rate in capillary electrophoresis by employing pressure to adjust velocity without unacceptably increasing plate height. Thus, the system controls bulk flow over a range of velocities, independent of the chemistry of the system.

The present invention employs a pressure differential between the inlet and outlet ports of the capillary which pressure differential can vary or remain constant over the duration of the electrophoretic run, to drive bulk flow in one direction or another. The pressure can go in the same or opposite direction to either the electrophoretic flow or the electroosmotic flow, depending on whether the goal is to increase or decrease the time period during which the charged particles stay in the capillary. The inlet port pressure could be generated by an air pump, while the outlet port is at atmospheric pressure. The pressure differential can encourage flow with or against the electroosmotic flow.

As previously discussed, plate height is a measure of the sharpness of the flow front as detected by a detector, where a lower plate height corresponds to a sharper flow front. Although differential pressure has been avoided in capillary electrophoresis because it degrades resolution and separation, it was found that the use of pressure in conjunction with electroosmotic flow causes only a minimal increase in plate height over that of electroosmotic flow alone, while giving the user considerable control over the bulk velocity. Thus, the present invention, which employs differential pressure in conjunction with electroosmotic flow in capillary electrophoresis, allows control over bulk velocity with minimal loss of resolution in terms of plate height.

BRIEF DESCRIPTION OF THE DRAWINGS

The present invention can be further understood with reference to the following description in conjunction with the appended drawings. In the drawings:

FIG. 1 is a functional diagram that schematically shows a capillary electrophoresis system in accordance with the present invention;

FIG. 2 is a graph showing velocity versus plate height for the molecule dimethylsulfoxide (DMSO) without any pressure, using purely osmotic separation at pH 7.0;

FIG. 3 is a graph showing the effect of differential pressure on the velocity and plate height of DMSO at pH 7.0; and FIG. 4 is a graph showing the effect of pressure in improving flow profile in capillary electrophoresis at pH 2.7.

DETAILED DESCRIPTION OF THE PREFERRED EMBODIMENTS

In FIG. 1, an electrophoretic system 10 includes a conventional capillary tube 12 having an inlet end 14 and an outlet end 16. The capillary tube can be, for instance, a fused silica tube having a coating of polyimide, with the polyimide coating being removed at one section of the tube. Typically, the capillary tube has an inside diameter of about fifty microns (0.05 mm), but dimensions in the range of 0.010 to 0.150 mm may be used.

As further shown in FIG. 1, a detector 18 is located at an intermediate position along the capillary tube 12 for detecting movement of materials within the tube. In conventional capillary zone electrophoresis, ultraviolet absorbance detectors are commonly used. At one side of the detector 18 is a mounted a buffer reservoir vial 24 that is in fluid communication with the outlet end 16 of the capillary tube 12. In the embodiment shown, the buffer reservoir vial is housed within a container 26.

The inlet end 14 of the capillary tube 12 is connected in fluid flow communication with a container 20 that includes a sample vial 22.

A first power supply 30 is electrically connected to the supply vial 22 via a conductor 32 that represents an anode electrode. The first power supply 30 provides a voltage, shown in FIG. 1 as −10 k volts, at the supply vial 22. It should be understood that this voltage is not the potential difference across the length of the capillary tube 12. The potential difference is determined by a voltage at the buffer reservoir vial 24. This voltage is provided by a second power supply 34 in electrical communication with the buffer reservoir vial 24 via a conductor 36 that represents the cathode electrode. In FIG. 1, the second power supply 34 is shown as providing a voltage of −15 k volts. Thus, the potential difference across the length of the capillary tube 12 is 5 k volts. A common potential gradient in capillary zone electrophoresis is 200 v/cm. To achieve this standard, the length of the capillary tube 12 would then be 25 cm. It should be noted that, although two power supplies are shown in FIG. 1, one of the power supplies can be replaced by ground.

In practice the voltage power supplies 30 and 34 have polarity-select switches 38 and 40 for adjusting the polarity of the associated electrodes 32 and 36. The voltage-adjustment vials 42 and 44 allow the outputs of the power supplies to be precisely set.

Container 20 has a sealed top 50 with a port 52 which is connected via tubing 54 to air pump 56. This configuration allows the application of pressure, vacuum or neither (i.e. atmospheric pressure) to sample vial 22. Similarly, reservoir vial 24 has a sealed top 60 with a port 62 which is connected via tubing 64 to air pump 66. Thus, pressure or vacuum can be applied to either end of the capillary and either end can be at atmospheric pressure.

At this juncture, it should be understood that the use of pressure in conventional capillary electrophoresis systems has been avoided as part of the separation system because it was thought that pressure differentials would degrade the resolution or separation of the molecules to be detected. However, pressure differentials for the system of the present invention are intentionally and controllably generated. In practice, the pressure differentials can be generated in several ways. For example, the pressure differential can be generated by an air pump, a water column, siphoning, vacuum, or other means known to those of skill in the art. It should be noted that the direction of differential pressure is not critical.

FIG. 2 shows a series of curves that resulted from an experiment which was conducted for determining the effect of pressure on the plate height and velocity of the capillary electrophoresis system. In the graph, the lower curve 70 depicts the theoretical limit for DMSO based only on its diffusion. This migration is due solely to electroosmotic forces, with no pressure being applied. The upper curve 72 shows the theoretical plot of plate height versus velocity if the system is only pressure driven. Actual experimental data points for DMSO without pressure are shown, and it can be noted that the data corresponds well with the theoretical limit based on electroosmosis alone.

FIG. 3 shows the results of experiments conducted using a capillary electrophoresis system with a differential pressure of 20 centimeters of water. Again, the lowest curve 80 represents the theoretical limit for DMSO based on its diffusion and the upper curve 82 represents the theoretical values for DMSO based only on pressure. The intermediate curve 84 represents the predicted values of plate height versus velocity with a differential pressure of 20 cm water head. As can be seen from the experimental values, the results for a capillary electrophoresis system using DMSO with 20 centimeters of pressure show that plate height is not significantly increased. This was true regardless of the direction of the pressure differential in this experiment. Thus, it can be understood that differential pressure can be used in a capillary electrophoresis system to increase the velocity without resulting in an unacceptably increased plate height.

These studies were conducted using a capillary electrophoresis system which employed a fused silica capillary of 0.05 mm I.D. and 40 cm length with fields ranging from 5 kv/40 cm to 25 kv/40 cm using phosphate buffer at pH 7.0.

FIG. 4 depicts the results of a study which was conducted using DMSO in a 0.05 mm I.D. fused silica capillary of 40 cm length with a field of 20 kv/40 cm. In the study, phosphate buffer of pH 2.7 was used. Under conditions of low pH, electroosmotic flow results in increased plate height. Again, lower curve 90 represents theoretical limits for electroosmotic flow only and upper curve 92 represents the theoretical value for pressure only. As shown in FIG. 4, the plate height under these conditions was about 0.015 mm at velocity of about 1.1 mm/sec. The application of 10, 20 or 30 cm of positive pressure actually decreased the plate height to about 0.011, 0.012, and 0.014 mm, respectively, thus improving the resolution.

As mentioned above, capillary electrophoresis systems of the present invention can employ various kinds of detectors. Detection can occur using an ultraviolet, chemiluminescence, refractive index, concentration sensitive, electrical, or conductivity detector. Any detector which can sense a concentration of the desired substance on the column can be used. Thus, the detector to be used is dependent on the molecule to be detected in the capillary electrophoresis system. Appropriate detectors are well known to those of skill in the art.

The double layer thickness (the inverse of Debye length) is a measure of where the electric potential of the inside of the capillary falls off to 63% of maximum. These wall effects are dependent on the chemistry of the system. In systems of the present invention, double layer thicknesses on the order of 0.2 to 10 nm are common.

Control of the electroosmotic flow of a capillary electrophoresis system can also be used in conjunction with pressure for improved bulk flow control. As discussed above, various kinds of control systems for electroosmotic flow can be employed. The method of this invention can be used in conjunction with an electroosmotic flow controller, but control of electroosmotic flow is not needed to apply the method of the present invention. Thus, the use of pressure alone can be used as the bulk flow control method for a capillary electrophoresis system.

However, the advantages of the invention will be realized best when used in conjunction with electroosmotic flow control methods. This is due to the fact that the electroosmotic flow control methods cause an increase in the plate height, and, as FIG. 4 shows for low pH, the addition of pressure driven flow can reduce the plate height. The advantages of the invention are better realized at pH less than 7.0 and best realized when using low pH buffers (less than about pH 4.0), because in a normal capillary electroosmotic system this condition will cause the plate height to rise far about the optimum value (where diffusion is the only factor). In that case, the addition of pressure will improve the plate height, and consequently the resolution. In particular, the addition of downstream pressure, i.e., in the direction of flow, improves plate height under these conditions.

Although the separation capillary has been shown as a single capillary tube, the separation capillary can include more than one capillary column and can have more than one inlet.

In a capillary electrophoresis system according to the present invention, it was discovered that the use of a pressure differential to force flow through a capillary in conjunction with electroosmotic flow unexpectedly results in an average bulk flow velocity with a sharper flow front than is achieved by electroosmotic flow alone under certain conditions. The system of the present invention provides sharp flow fronts while maintaining control over the bulk velocity. Accordingly, it can be appreciated that the above-described invention provides improved control of bulk flow in capillary electrophoresis applications over a broad range of velocities, independent of the chemistry of the system. Moreover, pressure control is independent of voltage and independent of chemistry and is thus an independent way of controlling bulk flow in capillary electrophoretic systems. Thus, pressure control may be useful to reduce the plate height in any situation which perturbs the flow front. However, in practice, a parabolic flow front is formed (laminar flow) if pressure alone is used to force flow in a capillary. This flow front is not as sharp as electroosmotic flow alone, and gives rise to large plate heights.

The foregoing has described the principles, preferred embodiments and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of present invention as defined by the following claims.

What is claimed is:

1. A system for controlling the rate of bulk flow in capillary electrophoresis comprising:

a) a separation capillary having an inlet end and an outlet end;

b) upstream liquid containment means in fluid flow communication with said inlet end for introducing a solution to said separation capillary;

c) downstream liquid containment means in fluid flow communication with said outlet end for receiving a flow of said solution;

d) voltage means for applying voltage between said inlet end and said outlet end;

e) forward and reverse bulk flow driver effective for selectively driving the bulk flow in both a forward and reverse direction across the length of said capillary through application of differential pressure selectively in a forward and a reverse bulk flow direction across the length of said separation capillary concurrently with the applied voltage;

f) in which the internal diameter of the capillary ranges from 0.010 to 0.150 mm and the double-layer thickness ranges from 0.2 to 10 nm, such that a ratio between an internal radius of the capillary and a double-layer thickness is at least 500.

2. The system of claim 1 which includes a first and a second pressure means for applying pressure to said inlet end and said outlet end of said separation capillary.

3. The system of claim 1 further including pressure adjustment means for adjusting the pressure differential within said separation capillary.

4. The system of claim 1 wherein said means for applying differential pressure includes means for applying a vacuum.

5. The system of claim 1 further including means for adjusting electroosmotic flow within said separation capillary.

6. The system of claim 1 wherein said solution has pH less than 7.0.

7. The system of claim 1 wherein said solution has pH less than 4.0.

8. The system of claim 1 further including detector means connected to said capillary tube for detecting migration within said capillary tube.

9. A method of controlling the rate of bulk flow of a sample solution in capillary electrophoresis comprising:

a) providing a capillary electrophoresis apparatus having a flow region between an inlet and an outlet port of a capillary tube, in which the internal diameter of the capillary ranges from 0.010 to 0.150 mm and the double-layer thickness ranges from 0.2 to 10 nm, such that a ratio between an internal radius of the capillary and a double-layer thickness is at least 500;

b) inducing electroosmotic flow of a solution within said flow region;

c) applying a pressure differential selectively in a forward and a reverse bulk flow direction across said flow region; and d) concurrently electrophoretically separating constituents of said solution by means of differential voltage.

10. The method of claim 9 wherein said pressure differential is adjusted during said separating step.

11. The method of claim 9 further including the step of detecting spatial separation of said constituents.

12. A capillary electrophoresis system comprising:

a) a capillary tube having an inlet end for introducing a sample solution and an outlet end, in which the internal diameter of the capillary ranges from 0.010 to 0.150 mm and the double-layer thickness ranges from 0.2 to 10 nm, such that a ratio between an internal radius of the capillary and a double-layer thickness is at least 500;

b) means for inducing electroosmotic flow of a solution within said capillary tube;

c) means for adjusting the electroosmotic flow;

d) forward and reverse bulk flow driver effective for selectively driving the bulk flow in both a forward and reverse direction across the length of said capillary through application of differential pressure selectively in a forward and in a reverse bulk flow direction between said inlet end and said outlet end;

e) means for adjusting said pressure differential;

f) means for concurrently applying a potential gradient across the length of said capillary tube to induce spatial separation by electrophoretic migration of constituents of said sample solution; and g) means for detecting spatial separation of said constituents.

* * * * *